United States Patent
Bergande

(10) Patent No.: US 9,839,536 B2
(45) Date of Patent: *Dec. 12, 2017

(54) LEG PROSTHESIS

(71) Applicant: OSSUR HF, Reykjavik (IS)

(72) Inventor: Stefan Bergande, Beedenbostel (DE)

(73) Assignee: OSSUR HF, Reykjavik (IS)

( * ) Notice: Subject to any disclaimer, the term of this patent is extended or adjusted under 35 U.S.C. 154(b) by 66 days.

This patent is subject to a terminal disclaimer.

(21) Appl. No.: 14/463,229

(22) Filed: Aug. 19, 2014

(65) Prior Publication Data

US 2014/0358249 A1 Dec. 4, 2014

Related U.S. Application Data

(63) Continuation of application No. 13/419,113, filed on Mar. 13, 2012, now Pat. No. 8,808,393.

(30) Foreign Application Priority Data

Mar. 15, 2011 (DE) .................. 10 2011 013 970

(51) Int. Cl.
*A61F 2/62* (2006.01)
*A61F 2/76* (2006.01)
(Continued)

(52) U.S. Cl.
CPC .................. *A61F 2/80* (2013.01); *A61F 2/76* (2013.01); *A61F 2/78* (2013.01);
(Continued)

(58) Field of Classification Search
CPC ...... A61F 2002/5018; A61F 2002/5021; A61F 2002/5023; A61F 2002/5083
(Continued)

(56) References Cited

U.S. PATENT DOCUMENTS 5,405,406 A * 4/1995 Hiemisch .................. A61F 2/76
403/90
5,507,837 A 4/1996 Laghi
(Continued)

FOREIGN PATENT DOCUMENTS

DE 10 2006 021 064 A1 11/2007
RU 2 475 214 C2 2/2013
WO 98/43559 A1 10/1998

OTHER PUBLICATIONS

Alpha Locking Lanyard Fabrication Instructions, published by Ohio Willow Wood on Aug. 11, 2003.*

*Primary Examiner* — David H Willse
(74) *Attorney, Agent, or Firm* — Workman Nydegger

(57) ABSTRACT

A leg prosthesis wherein the prosthesis shaft and the transtibial part are connected by a prosthesis shaft adapter. The prosthesis shaft adapter is constructed as a compact one-part component with a liner (sleeve as inner prosthesis shaft adapter) of the amputation stump and with a rearward extension for the prosthesis receptacle connection. The prosthesis shaft adapter is designed such that, in addition to the rearward extension of 1 cm to 10 cm, the prosthesis receptacle connection is also angled and laterally offset. Advantageously, the leg prosthesis according to the invention has a relatively low weight due to the prosthesis shaft adapter as a connecting element. The leg prosthesis operates absolutely safely and can be efficiently produced. The fabrication of a leg prosthesis with an individual biomechanical fit to the patient is significantly facilitated, which also results in fewer faulty prostheses.

13 Claims, 4 Drawing Sheets

Figure 1:
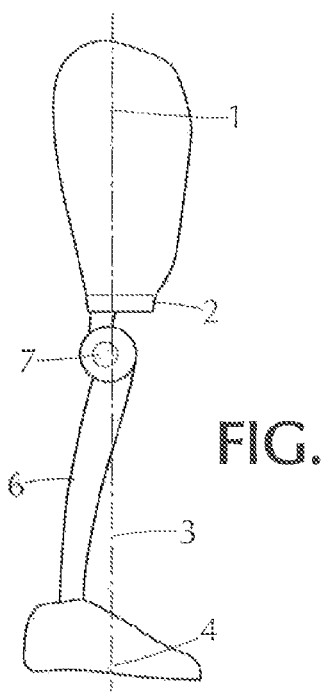

(51) Int. Cl.
 *A61F 2/80* (2006.01)
 *A61F 2/78* (2006.01)
 *A61F 2/50* (2006.01)

(52) U.S. Cl.
 CPC ............... *A61F 2002/5018* (2013.01); *A61F 2002/5023* (2013.01); *A61F 2002/5083* (2013.01)

(58) Field of Classification Search
 USPC ...................................... 623/33, 38; 403/90
 See application file for complete search history.

(56) References Cited

U.S. PATENT DOCUMENTS

| | | | |
|---|---|---|---|
| 5,888,234 | A | 3/1999 | Littig |
| 6,991,658 | B2 | 1/2006 | Slemker et al. |
| 7,083,654 | B2 | 8/2006 | Helenberger et al. |
| 8,192,503 | B2 * | 6/2012 | Olafsson et al. ............... 623/38 |
| 2002/0193887 | A1 | 12/2002 | Swanson, Sr. |
| 2007/0260329 | A1 | 11/2007 | Hiemisch |
| 2011/0015761 | A1 | 1/2011 | Celebi et al. |
| 2012/0259432 | A1 * | 10/2012 | Dillingham ............... A61F 2/60 623/31 |

* cited by examiner

LEG PROSTHESIS

BACKGROUND OF THE INVENTION (1) Field of the Invention

The invention relates to a leg prosthesis, consisting of a prosthesis shaft with a prosthesis shaft adapter non-releasably integrated therein and a transtibial part with a foot and a knee joint part or a transtibial part with a foot, wherein the prosthesis shaft and the transtibial part are releasably connected with each other by way of the prosthesis shaft adapter.

(2) Description of Related Art

Leg prostheses and prosthesis shaft adapters producing a suitable mechanical connection between the prosthesis shaft and the transtibial part of a leg prosthesis are known. Frequently, a so-called inner shaft, or liner, made of a soft flexible material, for example silicone, is used in the hollow space of the prosthesis shaft for direct skin contact and as adhesion promoter on the skin. The lower closed end of the liner has a metal pin which is connected to the liner over a large area, wherein the pin can be locked with the liner though an opening in the lower prosthesis part and fixed in this position.

For applying the liner on the amputation stump, the liner is rolled up on the amputation stump and then inserted into the actual prosthesis shaft and connected and locked by the metal pin with an adapter in or on the prosthesis shaft for securing the liner on the knee joint component.

For removing the liner, the lock is released again and the amputation stump with the liner is pulled out of the prosthesis shaft and rolled down.

For realizing this mechanical process, at least one additional adapter is required on the alignment line between the hip joint and the midfoot for vertical biostatic force flux equalization. In practice, however, several adapters are frequently required for shifting the coupling location or the connection location to the knee joint of the transtibial part back.

Disadvantageously, in particular when several adapters are required for shifting or returning the connection between the prosthesis shaft and the knee joint of the transtibial part due to the size of the patient and the length of the amputation stump as well as due to the biostatic. However, the overall height is determined by the patient and is frequently not adequate for the system to enable a proper fit. Alternatively, very expensive custom-built designs need to be considered.

When using several adapters, their relatively high weight and an increased accident risk due to the large number of components and the costs for these components are disadvantageous (U.S. Pat. No. 5,888,234; U.S. Pat. No. 5,507,837; U.S. Pat. No. 7,083,654; US 2011-0015761 A1).

BRIEF SUMMARY OF THE INVENTION

It is an object of the invention to provide a leg prosthesis with a prosthesis adapter having minimal height, minimal weight and a small number of components that can be easily handled and operates safely, which has a structure that can be adapted and used universally and individually. Trained personnel producing prostheses should be able to efficiently, easily and inexpensively fabricate the prosthesis adapter.

According to the invention, this object is attained with the recited claims.

The basic structure of the prosthesis shaft adapter of the leg prosthesis for forming a custom-fit connection between the prosthesis shaft and the transtibial part is hereby formed as a compact one-piece component. The prosthesis shaft adapter is, on one hand, designed with an integrated amputation stump receiving cup with or without connection mechanism and locking mechanism for the liner (sleeve as inner prosthesis adapter), such as a Velcro tape lock, a drawstring or safety pin lock, or a connection of the amputation stump with a vacuum pump and vacuum control valves on the amputation stump.

On the other hand, the prosthesis shaft adapter is constructed with an integrated rearward extension A, i.e. rearward relative to the walk direction line, to provide a spacing from the amputation stump cup and a prosthesis receptacle connection for the transtibial part or a screwable knee joint assembly.

The prosthesis shaft adapter is herein dimensioned such that the rearward extension A with spacing between the centerline (center) of the amputation stump cup in the prosthesis shaft adapter and center of the prosthesis receptacle connection can be 1 cm to 10 cm. The prosthesis receptacle connection is hereby designed such that the centerline of the attached transtibial part 6 or of the knee joint assembly extends in relation to the centerline of the cup and an imaginary vertical alignment line 3 from the hip joint to the midfoot at an acute angle a from 5° to 20°.

In another embodiment, the prosthesis receptacle connection of the rearward extension A may also be offset to the side, by an offset B, from the walk direction line, so that in addition to the rearward extension A also a sideways displacement of the prosthesis receptacle connection 10 can be implemented with the offset B to a walk direction line parallel to the walk direction line.

The prosthesis shaft adapter is herein dimensioned such that the rearward extension A with spacing between the center of the amputation stump cup in the prosthesis shaft adapter and the center of the prosthesis receptacle connection 10 may be 1 cm to 10 cm, with the lateral offset B potentially reaching ±6 cm.

The prosthesis receptacle connection for attachment of the transtibial part or the knee joint assembly may be a flange connection with the flange, an axial screw connection with a thread, a bayonet connection or a non-releasable connection.

Advantageously, the leg prosthesis according to the invention has a prosthesis shaft adapter of significantly less weight than other comparable prosthesis shaft adapters and consists of only a single compact component. The leg prosthesis can be optimally biokinetically fitted to the patients with the prosthesis shaft adapter, in particular also due to the lateral offset in relation to the walk line.

The prosthesis shaft adapter operates absolutely safely and maintenance-free by minimizing components, such as screws, etc., and can be produced efficiently. An orthopedic technician can much more easily fabricate these leg prostheses with an excellent individual biomechanical fit to the patient, which also helps to prevent a faulty fabrication.

The invention will now be described with reference to two exemplary embodiments.

BRIEF DESCRIPTION OF THE SEVERAL VIEWS OF THE DRAWING(S)

The appended drawing shows in

Figure 2:
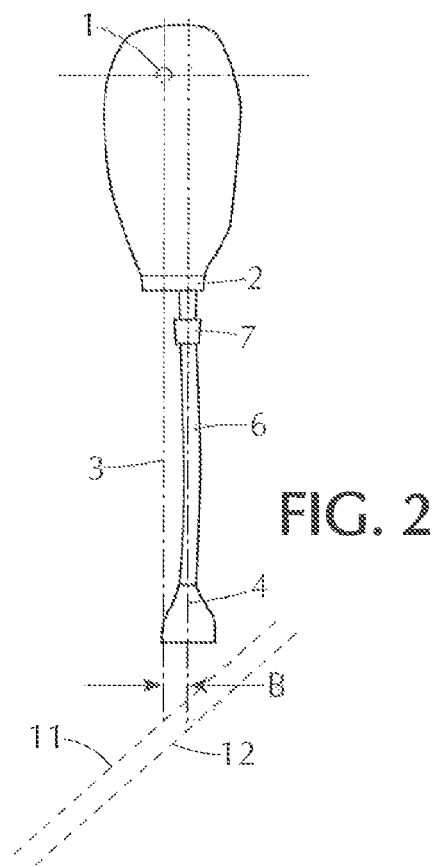
Figure 3:
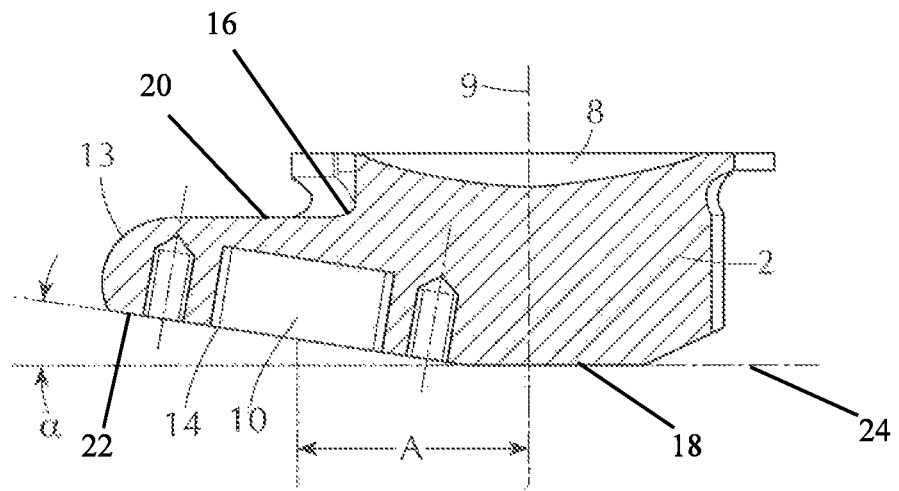
Figure 4:
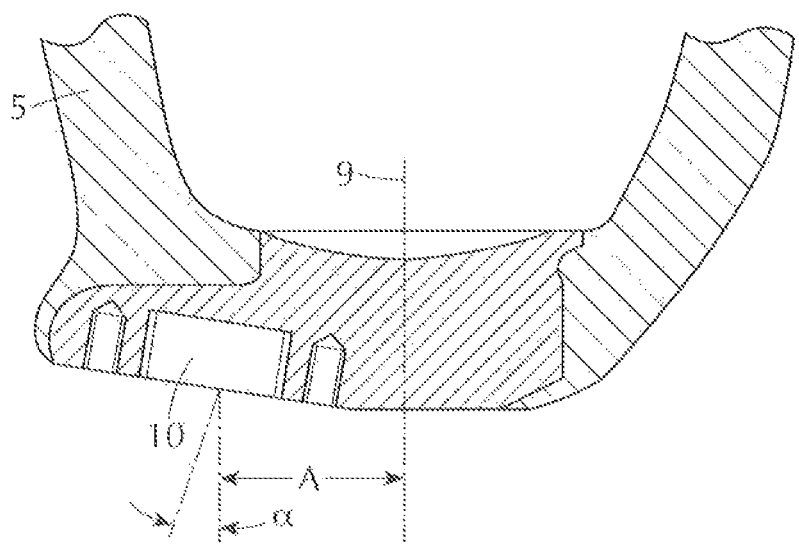
Figure 5:
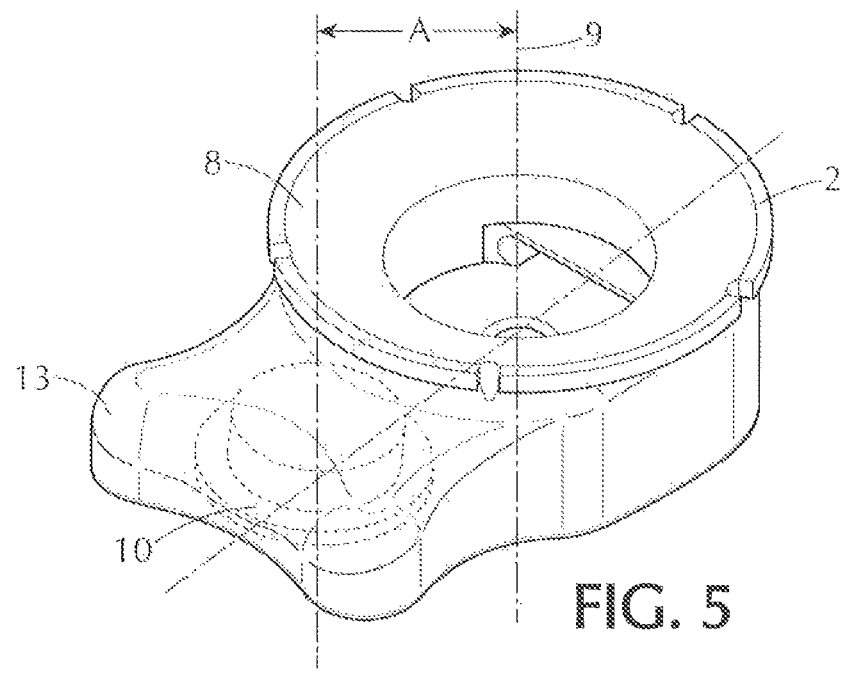
Figure 6:
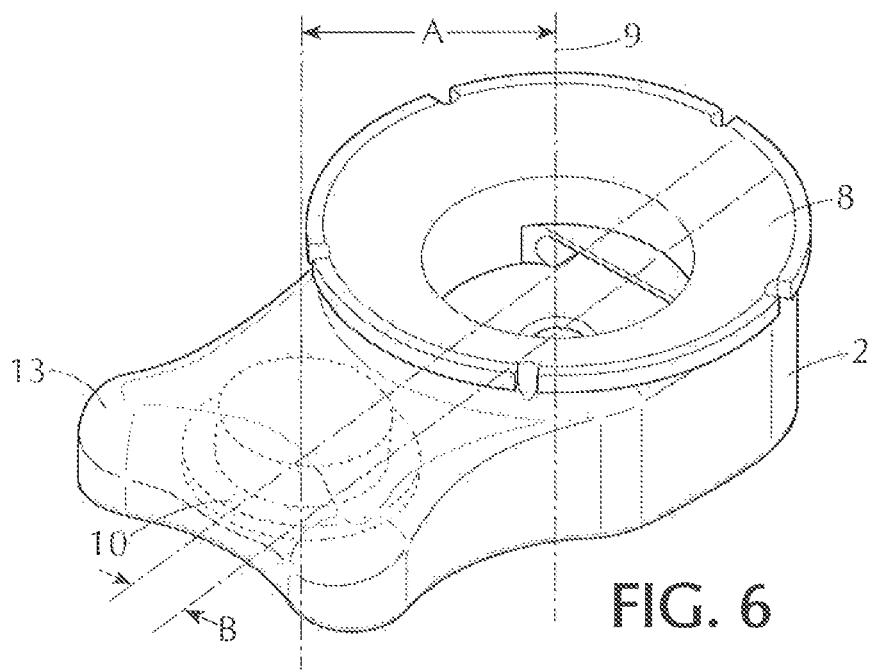
Figure 7:
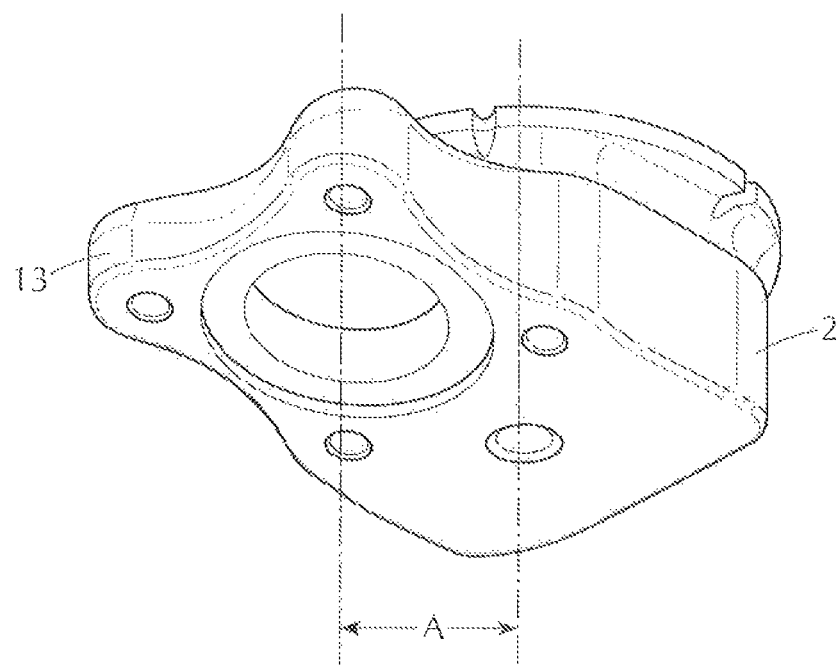

FIG. 1 a leg prosthesis with a prosthesis shaft, a prosthesis shaft adapter assembly and a transtibial part in a side view, FIG. 2 a leg prosthesis with a prosthesis shaft, a prosthesis shaft adapter assembly and a transtibial part in a front view, FIG. 3 a prosthesis shaft adapter in cross-section, FIG. 4 a prosthesis shaft adapter formed in the prosthesis shaft in cross-section, FIG. 5 a prosthesis shaft adapter in a perspective top view, FIG. 6 a prosthesis shaft adapter with a lateral offset, and FIG. 7 a schematic diagram of a prosthesis shaft adapter in a perspective bottom view.

DETAILED DESCRIPTION OF THE INVENTION

In one embodiment, the basic structure of the prosthesis shaft adapter 2 of the leg prosthesis for forming a custom-fit connection between the prosthesis shaft 5 and the transtibial part 6 is hereby formed as a compact one-piece component. The prosthesis shaft adapter 2 is, on one hand, designed with an integrated amputation stump receiving cup 8 with or without connection mechanism and locking mechanism for the liner (sleeve as inner prosthesis adapter), such as a Velcro tape lock, a drawstring or safety pin lock, or a connection of the amputation stump with a vacuum pump and vacuum control valves on the amputation stump.

On the other hand, the prosthesis shaft adapter 2 is constructed with an integrated rearward extension A, i.e. rearward relative to the walk direction line, to provide a spacing from the amputation stump cup 8 and a prosthesis receptacle connection 10 for the transtibial part 6 or a screwable knee joint assembly 7.

The prosthesis shaft adapter 2 is herein dimensioned such that the rearward extension A with spacing between the centerline 9 (center) of the amputation stump cup 8 in the prosthesis shaft adapter 2 and center of the prosthesis receptacle connection 10 can be 1 cm to 10 cm.

The prosthesis receptacle connection 10 is hereby designed such that the centerline of the attached transtibial part 6 or of the knee joint assembly 7 extends in relation to the centerline 9 of the cup and an imaginary vertical alignment line 3 from the hip joint 1 to the midfoot 4 at an acute angle α from 5° to 20° such that a segment 22 of the second side of the prosthesis shaft adapter 2 at the extension A or flange 13 is arranged at the acute angle α relative to a segment 18 of the second side of the prosthesis shaft adapter 2 below the receiving cup 8. The segment 18 is located along horizontal line 24. A segment 20 of the first side of the prosthesis shaft adapter 2 at the extension A or the flange 13 is generally parallel to the segment 18 of second side of the prosthesis shaft adapter 2. The segment 20 of the first side of the prosthesis shaft adapter 2 at the extension A or the flange 13 is arranged generally at a right angle 16 relative to the centerline 9.

In another embodiment, the prosthesis receptacle connection 10 of the rearward extension A may also be offset to the side, by an offset B, from the walk direction line 12, so that in addition to the rearward extension A also a sideways displacement of the prosthesis receptacle connection 10 can be implemented with the offset B to a offset walk direction line 11 parallel to the walk direction line 12.

The prosthesis shaft adapter 2 is herein dimensioned such that the rearward extension A with spacing between the center 9 of the amputation stump cup 8 in the prosthesis shaft adapter 2 and the center of the prosthesis receptacle connection 10 may be 1 cm to 10 cm, with the lateral offset B potentially reaching ±6 cm.

The prosthesis receptacle connection 10 for attachment of the transtibial part 6 or the knee joint assembly 7 may be a flange connection with the flange 13, an axial screw connection with a thread 14, a bayonet connection or a non-releasable connection.

Advantageously, the leg prosthesis according to the invention has a prosthesis shaft adapter of significantly less weight than other comparable prosthesis shaft adapters and consists of only a single compact component. The leg prosthesis can be optimally biokinetically fitted to the patients with the prosthesis shaft adapter, in particular also due to the lateral offset in relation to the walk line.

The prosthesis shaft adapter operates absolutely safely and maintenance-free by minimizing components, such as screws, etc., and can be produced efficiently. An orthopedic technician can much more easily fabricate these leg prostheses with an excellent individual biomechanical fit to the patient, which also helps to prevent a faulty fabrication.

Example 1

For fabricating an individual leg prosthesis for a femoral amputation stump, the orthopedic technician initially measures and determines according to the alignment line 3 from the hip joint 1 to the midfoot 4 a prosthesis shaft adapter 2 according to the invention in accordance with biomechanical criteria with respect to a measured required rearward extension A of 5 cm on a walk direction line 12 without a lateral offset B and an angle of its prosthesis receptacle connection 10 of 9°, and selects a flange connection with flange fitting 14 as the prosthesis receptacle connection 10.

The prosthesis shaft adapter 2 determined in this manner is then formed fixedly and non-releasably in the lower part of the prosthesis shaft 5 such that the prosthesis receptacle connection 10 for the transtibial part 6 is exposed and accessible for its installation or the installation of its knee joint assembly 7. The installation is then performed in a conventional manner. With the rearward extension A and the angle of the transtibial receptacle connection 10, a leg prosthesis according to biomechanical criteria can be optimally realized.

Example 2

For fabricating an individual leg prosthesis for a femoral amputation stump, the orthopedic technician initially measures and determines a prosthesis shaft adapter 2 according to the invention with respect to a measured required rearward extension A of 7 cm and an angle of its prosthesis receptacle connection 10 of 15° and a lateral offset B of 4 cm in accordance with biomechanical criteria, and selects a screw connection with an interior thread 14 as the connection between the prosthesis shaft adapter 2 and the transtibial part 6.

The prosthesis shaft adapter 2 determined in this manner is then formed fixedly and non-releasably in the lower part of the prosthesis shaft 5 such that the prosthesis receptacle connection 10 for the transtibial part 6 is exposed and accessible for its installation or the installation of its knee joint assembly 7.

The installation is then performed in a conventional manner. With the rearward extension A and the angle of the transtibial receptacle connection 10 and the lateral offset B, a leg prosthesis according to biomechanical criteria can be optimally realized.

The invention claimed is:

1. A prosthesis shaft adapter, comprising:
a compact, monolithic component including a main body and an extension projecting rearward from the main body, the main body defining a receiving cup formed on a first side of the main body and having a vertical centerline, and the extension defining a receptacle formed on a second side of the main body opposite the receiving cup, the extension extending and aligned along a walk direction line, wherein the vertical centerline is located along the walk direction line and perpendicular thereto;

wherein the extension extends at a right angle relative to a surface of the receiving cup;

wherein the receptacle is offset to a lateral side by an offset B from the walk direction line, such that the location of the receptacle is defined with the offset B to an offset walk direction line parallel to the walk direction line;

wherein the extension is arranged at an acute angle from 5 to 20 degrees relative to the centerline of the receiving cup and an imaginary vertical alignment line defined from a hip joint and a midfoot, the vertical centerline and the imaginary vertical alignment line are parallel to one another;

wherein a segment of a second side of the extension is arranged at the acute angle relative to a segment of the second side of the main body below the receiving cup and along a horizontal line, a segment of a first side of the extension opposite a second side of the extension is generally parallel to the horizontal line, the segment of the first side of the extension is arranged generally at a right angle relative to the vertical centerline.

2. The prosthesis shaft adapter of claim 1, wherein the receptacle is centrally formed on the extension.

3. The prosthesis shaft adapter of claim 1, wherein the receptacle extends through the extension.

4. The prosthesis shaft adapter of claim 1, wherein the extension is arranged parallel to the walk direction line and laterally offset relative thereto.

5. The prosthesis shaft adapter of claim 1, wherein the extension extends at a right angle relative to a surface of the receiving cup such that a distance between the centerlines of the receiving cup and the receptacle is in the range of 1 to 10 cm.

6. The prosthesis shaft adapter of claim 1, wherein the centerline of the receptacle is laterally offset relative to the walk direction line in the range of 4 to 6 cm.

7. The prosthesis shaft adapter of claim 1, wherein the extension is flange projecting from the main body and has a smaller thickness than the main body.

8. The prosthesis shaft adapter of claim 1, wherein the receptacle includes a connection selected from the group consisting an axial screw connection, a bayonet connection and a non-releasable connection.

9. A leg prosthesis comprising:
a prosthetic shaft;
a prosthesis shaft adapter fixedly and non-releasably secured to a lower portion of the prosthesis shaft, the prosthesis shaft adapter comprising a compact, monolithic component including a main body and an extension projecting linearly rearward from the main body, the main body defining a receiving cup having a vertical centerline and the extension defining a receptacle having a centerline, the extension arranged along a walk direction line, wherein the receptacle is offset to a lateral side by an offset B from the walk direction line, such that the receptacle is located by the offset B to an offset walk direction line parallel to the walk direction line;

wherein the prosthetic shaft defines an opening, and the prosthesis shaft adapter is disposed entirely within the opening;

wherein the extension extends at a right angle relative to a surface of the receiving cup such that a distance between the centerlines of the receiving cup and the receptacle is in the range of 1 to 10 cm;

wherein a segment of a second side of the extension is arranged at an acute angle relative to a segment of a second side of the main body below the receiving cup and along a horizontal line, a segment of a first side of the extension opposite the second side of the extension is generally parallel to the horizontal line, the segment of the first side of the extension is arranged generally at the right angle relative to the vertical centerline;

wherein the extension is arranged at an acute angle from 5 to 20 degrees relative to the vertical centerline of the receiving cup and an imaginary vertical alignment line defined from a hip joint and a midfoot, the vertical centerline and the imaginary vertical alignment line are parallel to one another.

10. The leg prosthesis of claim 9, wherein the centerline of the receptacle is arranged at an acute angle relative to the centerline of the receiving cup.

11. The leg prosthesis of claim 10, wherein the acute angle is in the range of 5 to 20 degrees.

12. The leg prosthesis of claim 9, wherein the centerline of the receptacle is laterally offset relative to the walk direction line in the range of 4 to 6 cm.

13. A leg prosthesis comprising:
a prosthetic shaft;
a prosthesis shaft adapter fixedly and non-releasably secured to a lower portion of the prosthesis shaft, the prosthesis shaft adapter comprising a compact, monolithic component including a main body and an extension projecting linearly rearward from the main body, the main body defining a receiving cup having a vertical centerline and the extension defining a receptacle having a centerline, the extension arranged along a walk direction line and the receptacle defined along a surface of the adapter opposite to a surface defining the receiving cup;

wherein the extension extends at a right angle relative to a surface of the receiving cup;

wherein the vertical centerline is located along the walk direction line and perpendicular thereto;

wherein the prosthetic shaft defines an opening, and the prosthesis shaft adapter is disposed entirely within the opening with the receptacle accessible from under the prosthetic shaft;

wherein the extension is arranged at an acute angle from 5 to 20 degrees relative to the vertical centerline of the receiving cup and an imaginary vertical alignment line defined from a hip joint and a midfoot, the vertical centerline and the imaginary vertical alignment line are parallel to one another;

wherein a segment of a second side of the extension is arranged at the acute angle relative to a segment of the second side of the main body below the receiving cup and along a horizontal line, a segment of a first side of the extension opposite a second side of the extension is generally parallel to the horizontal line, the segment of the first side of the extension is arranged generally at a right angle relative to the vertical centerline.

* * * * *